Figure 1:
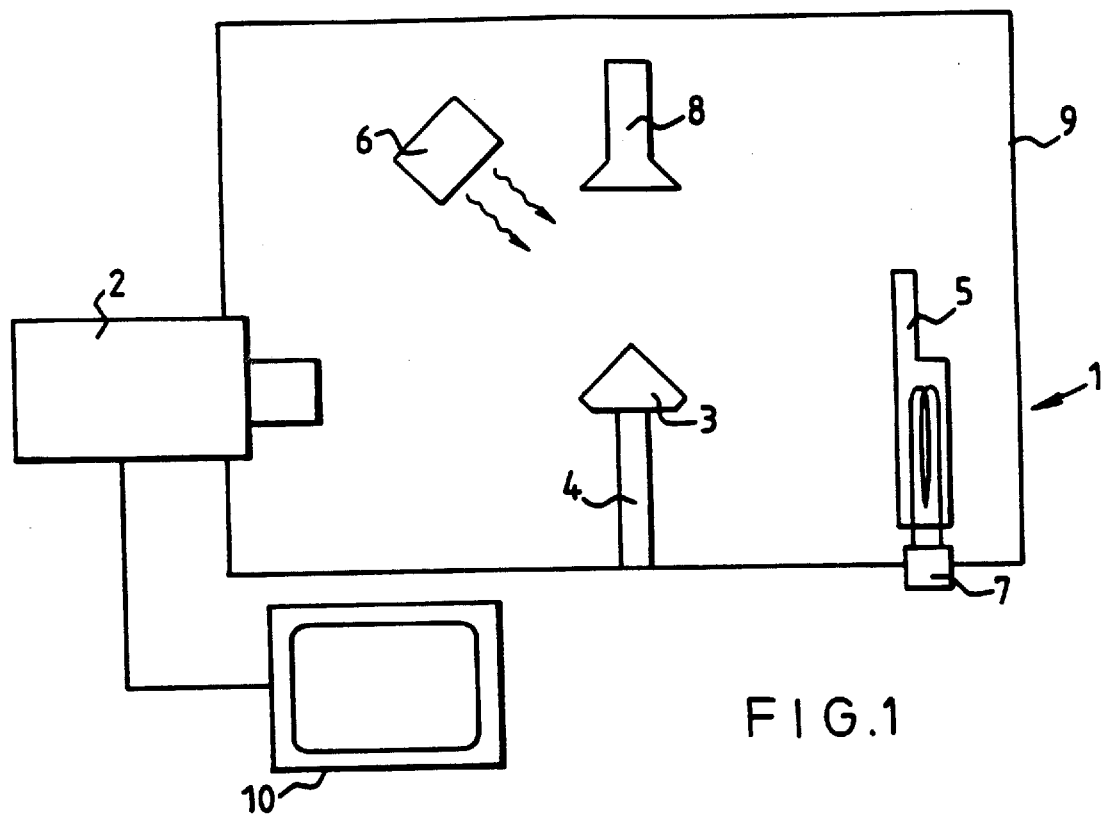

United States Patent
Smith et al.

[11] Patent Number: 5,883,388
[45] Date of Patent: Mar. 16, 1999

[54] EXAMINING A DIAMOND

[75] Inventors: Martin Phillip Smith, Wargrave; James Gordon Charters Smith, High Wycombe; Martin Cooper, Marlow; Ricardo Simon Sussmann, Guildford, all of United Kingdom

[73] Assignee: Gersan Establishment, Liechtenstein

[21] Appl. No.: 809,150

[22] PCT Filed: Sep. 5, 1995

[86] PCT No.: PCT/GB95/02092

§ 371 Date: Jun. 19, 1997

§ 102(e) Date: Jun. 19, 1997

[87] PCT Pub. No.: WO96/07895

PCT Pub. Date: Mar. 14, 1996

[30] Foreign Application Priority Data

Sep. 7, 1994 [GB] United Kingdom .................. 9418050

[51] Int. Cl.$^6$ ................................................ G01N 21/87
[52] U.S. Cl. ............................................ 250/330; 356/30
[58] Field of Search ................................ 356/30; 250/330

[56] References Cited

U.S. PATENT DOCUMENTS

| 3,721,289 | 3/1973 | Seal . | |
|---|---|---|---|
| 4,875,771 | 10/1989 | Bowley et al. | 356/30 |
| 4,915,827 | 4/1990 | Rosenthal . | |
| 5,386,117 | 1/1995 | Piety et al. | 250/330 |
| 5,396,068 | 3/1995 | Bethea | 250/330 |

FOREIGN PATENT DOCUMENTS

| 0 064 842 | 11/1982 | European Pat. Off. . |
| 0 425 426 | 5/1991 | European Pat. Off. . |
| 80 4432 | 7/1980 | South Africa . |
| 2 076 146 | 11/1981 | United Kingdom . |
| 83/00389 | 2/1983 | WIPO . |

Primary Examiner—Constantine Hannaher
Attorney, Agent, or Firm—Cesari and McKenna, LLP

[57] ABSTRACT

In order to test whether a diamond has had a layer of synthetic diamond material deposited thereon, infrared radiation including radiation of wavelength substantially 7 $\mu$m to 25 $\mu$m preferably 7 $\mu$m to 10 $\mu$m emitted or transmitted by the diamond is observed, to detect differences between the compositions of different zones of the diamond.

47 Claims, 1 Drawing Sheet

EXAMINING A DIAMOND

BACKGROUND OF THE INVENTION

The present invention relates to a method of and apparatus for examining a diamond. For example, the invention may be used to test whether a diamond has had a layer of synthetic diamond deposited thereon. This is of particular importance in detecting whether the diamond comprises CVD diamond material and also in locating such material if present.

The synthetic diamond material may be deposited on an uncut or part-worked natural diamond which is then worked, for example, into a round brilliant cut. Alternatively, the synthetic diamond coating may be deposited onto a fully fashioned brilliant stone after working of the stone. The thickness of the synthetic diamond material layer may be very thin—it could be in the range from 1 $\mu$m to 0.1 mm.

The value of a diamond is in part dependent upon its weight. Accordingly, synthetic diamond material may be deposited onto natural gem diamonds, before or after cutting of the diamond, to increase the weight of the finished product.

However, the value of a diamond also resides in its qualities of authenticity and uniqueness and in the fact that it is an entirely natural product. Thus, a diamond that has not been enlarged by deposition of synthetic diamond material has a value over a diamond that has.

Over the years, a number of methods of synthesising diamond material have been developed. One of these methods is the chemical vapor deposition (CVD) technique, which is a low pressure technique involving deposition of synthetic diamond (referred to as CVD diamond material in this specification) onto a substrate from a gas. CVD is the method which is most likely to be used to deposit synthetic diamond onto a diamond.

A diamond artificially enlarged by deposition of CVD diamond material is referred to in this specification as a "CVD/natural diamond doublet".

CVD diamond material may be deposited on a diamond substrate. The CVD diamond material can replicate the structure of the diamond substrate (referred to "homoepitaxial growth"). The CVD/natural diamond doublet produced can be identical in appearance, density and other common physical properties to an entirely natural stone and there may be a problem in identifying such a CVD/natural diamond doublet.

It is an object of the present invention to provide a method of and apparatus for determining whether a diamond has had a layer of synthetic diamond deposited thereon.

It is desired that the apparatus should be simple and inexpensive and may be put into operation by a person with relatively little training. The method and apparatus should be capable of being operated reliably and consistently by a practiced jeweller who has no training in laboratory gemological analysis.

THE INVENTION

The present invention provides a method of testing whether a diamond has had a layer of synthetic diamond deposited thereon, comprising comparing observations of infra red radiation emanating from each of a plurality of zones of the diamond, to detect differences between the compositions of different zones of the diamond, the radiation observed including radiation of wavelength substantially in the range 7 $\mu$m to 25 $\mu$m, preferably 7 $\mu$m to 10 $\mu$m.

The present invention also provides apparatus for testing whether a diamond has had a layer of synthetic diamond deposited thereon, comprising means for observing infra red radiation emanating from a zone of the diamond which is substantially smaller than the total surface area of the diamond, the radiation observed including radiation of wavelength substantially in the range 7 $\mu$m to 25 $\mu$m, preferably 7 $\mu$m to 10 $\mu$m.

The present inventors have discovered that where the intensity of infra red radiation of the abovementioned waveband emanating from a diamond is different between different zones, it may be concluded that the diamond has had a layer of synthetic diamond deposited thereon. Where there are no such differences, it may be concluded that the diamond is substantially of one type. Care should be taken, as explained below, to distinguish low observed intensities of radiation caused by internal reflection within the diamond from low observed intensities caused by different compositions of diamond.

The present inventors have further discovered that the observations of infra red radiation may be compared with similar observations for a diamond of known type, to indicate whether the diamond under test is of the same type as the known diamond. If the known diamond is type IaAB, the diamond under test can be classified as definitely natural (type IaAB) or not definitely natural, because type IaAB diamonds are always natural.

By "radiation emanating from a diamond" is meant radiation transmitted by the diamond, or emitted by the diamond, or both.

The present invention is based upon the observation that the majority of natural diamonds are type IaA or IaAB, whereas CVD diamond material is normally type II, which transmits infra red radiation more strongly than type IaAB and IaA diamond in the waveband 7 $\mu$m to 25 $\mu$m, the band of interest.

The present inventors have further discovered that observations of the infra red radiation emitted from a diamond in the band of interest can be used to detect a layer of synthetic diamond material deposited on a natural stone. It is simpler and more effective to observe emitted infra red radiation than transmitted radiation.

Preferably, a large number of zones of the diamond are observed, as CVD diamond material, if present, may be localized on a part of the surface of the diamond. An image may of course be thought of as composed of a plurality of zones.

Preferably, enough zones to cover substantially the whole surface of the diamond are observed.

A preferred method of observing a large number of zones of the diamond at once comprises forming an image of the infra red radiation emanating from the diamond. An image may of course be thought of as composed of a plurality of zones.

Preferably, the zones observed are small, being less than 1 mm, preferably less than 0.5 mm across. Where an image is formed, the size of the zones observed is only limited by the resolution of the imaging system.

An image of the diamond may be formed as viewed in a first direction relative to the diamond, at least one further image of the diamond being formed as viewed in a different direction relative to the diamond. In this way, zones not visible from the first direction may be examined. The normal to the interface of a synthetic diamond layer and natural stone should be substantially normal to the optical axis of the imaging means, in order to be detected.

Preferably, an image of the diamond is formed using a long-wavelength thermal imaging camera, for example an Agema 900 Series thermal imaging camera. Alternatively, an infra red imaging system having a cooled infra red filter passing radiation substantially in the waveband of interest may be used.

Image processing means may be provided to improve contrast between areas of different emissivity. For example, areas of different temperature range may be presented in different colours. In order to distinguish the thermal emission of the diamond from that of the background, the image of the diamond may be formed against a background at a different temperature to the diamond. A temperature difference in the range 5° to 50° C. may be used, preferably in the range 20° to 30° C. Such a temperature difference will give adequate distinction between the diamond and the background, without the problems associated with greater temperature differences.

Preferably, the diamond is at a higher temperature than the background, which may be achieved by heating the diamond or cooling the background, or both. However, the diamond could instead be cooled and/or the background heated.

The emission properties of the background in the waveband substantially 7 μm to 25 μm may be tailored to enhance the view taken. The background could be made of a very good infra red emitter (for example, a matt black material) or a very poor emitter (for example, a mirror-polished surface), instead of or in addition to being of a different temperature.

The diamond or background may be heated by being placed in contact with a heated support, by pre-heating it before placing it in the apparatus, by heating it in a warm air stream, or by using an infra red heating source or by a combination of these methods. If an infra red source is used, the source irradiation direction should not be coincident with the imaging direction, in order to avoid flooding the image of the diamond with background radiation.

The background or the diamond may be cooled by being placed in contact with a cool support, by pre-cooling or by directing cold air onto the surface of the diamond or background or by a combination of these methods.

All parts of the diamond should be at substantially the same temperature.

In order to assist the interpretation of the image of the diamond, the diamond may be irradiated with radiation which is substantially transmitted by all types of diamond, such as visible radiation, or which is transmitted by no type of diamond, such as radiation of wavelength less than 230 nm, so that a dark or light image of the entire diamond or a reference image may be formed. This reference image may then be compared to the image taken at the first mentioned wavelength, preferably with the diamond in the same configuration. The reference image can be used to distinguish features caused by different zones having different emissivity from artifacts caused by internal reflection of infra red radiation in the diamond. The reference image may be taken against a light background or against a dark background, and/or by irradiating the diamond with light in a different direction to the direction of imaging.

The infra red radiation emitted by a zone of the diamond may be observed by using radiation collecting means, such as a light guide (advantageously a fiber-optic probe) and a radiation detector to which the collected radiation is directed. Any suitable known type of apparatus for measuring the intensity of radiation emanating from the zone may be used.

If a fiber-optic probe is used, it may be fixed in means for mounting the diamond, different zones of the diamond being placed in contact with the end of the probe by manipulating the diamond. Any suitable known means may be used for mounting the diamond, such as a plinth or ledge. Alternatively, the diamond may be stationary and the fiber-optic probe manipulated around the diamond. When a light guide such as a fiber-optic probe is used, a "map" or crude image of the emissivity at different zones of the diamond may be produced by testing each such zone in turn. A crude image can be produced without expensive imaging apparatus. The apparatus in this form may be suitable for automation.

A plurality of fiber-optic probes may be used for contacting different zones of the diamond at the same time.

In order to avoid possible errors arising from poor or uncontrolled contact of the fiber-optic probe with a zone of the diamond, a plurality of observations at the same wavelength may be made for the same zone and combined statistically to provide a statistically improved reading.

Optical means may be provided to allow a visible check to ensure that the end of the probe is in contact with the desired zone of the diamond before the intensity of radiation emitted is observed.

When the diamond is imaged, the image formed may be interpreted by the operator by comparing the apparent intensity of emission of different parts of the diamond or the intensities of radiation emitted by different parts of the diamond may be measured and their differences calculated. Assuming that the diamond is at a substantially uniform temperature, parts of the diamond which have different infra red emissivity will appear to have different intensities of emission. Emissivity may be defined as the ratio of the power per unit area radiated by the surface to that radiated by a black body at the same temperature. Emissivity as a function of wavelength is defined as the ratio of the power per unit area per unit wavelength interval radiated by a surface at a given wavelength and temperature to that radiated by a black body at the same wavelength and temperature.

Synthetic diamond material deposited on a natural stone will have a lower emissivity than the neighboring natural diamond material and will appear to be cooler.

If a light guide is used to measure the intensity of radiation-emitted by a zone of the diamond, a signal dependent upon the emission intensity can be read directly for each of the zones. A fiber-optic probe may be used, being moved over the diamond to look for parts which have an abnormally low emission intensity.

The radiation observed may comprise a narrow band of wavelengths lying in the band of interest or a number of such narrow bands, but is preferably a relatively broad band lying substantially in the band of interest, as this maximizes the amount of radiation observed. The radiation studied may comprise radiation of wavelengths falling outside the above-mentioned range, for example as low as 6 μm or as high as 30 μm. It is preferred that the power of radiation falling within the band of interest will not be swamped out by radiation of wavelength falling outside this band.

It is strongly preferred that the radiation observed should include radiation falling substantially in the range 7 μm to 10 μm. In this range, the absorption coefficient of natural diamond is significantly higher (being three or more times higher) than that of synthetic diamond. Therefore, the contrast between the intensity of radiation emitted by natural and artificial diamond material is good. In the band 10 μm to 25 μm, the intensity of radiation emitted by a natural diamond is detectably larger than that emitted by artificial diamond. However, the difference is small and if this band is observed, the observing means should be very sensitive to small differences in intensity of radiation observed.

In a preferred embodiment, an emissivity difference of 0.5–5% or more, preferably 1% or more between different areas is interpreted to indicate that diamond material of different compositions is present.

The diamond may be observed using image processing means such as a computer. The image processing means may be set up to present the image using false colors to represent areas of different emission intensity bands. In this case, the threshold between the two emission intensity bands may be set such that areas of the diamond which are of different composition but which are otherwise identical in orientation, temperature, surface finish etc fall into different color bands. This will make visualization of areas of different composition easier.

The threshold may be set by the operator. For example, the operator could select an area of the image and program the image processing means to assign a different color to an area of the diamond having an emissivity difference of 0.5–5% or more, preferably 1% or more, from it.

It is possible to irradiate the diamond with infra red radiation and observe infra red radiation transmitted by different zones of the diamond, the observed radiation including radiation substantially of wavelength substantially 7 μm to 25 μm.

If some zones of the diamond under test transmit less infra red radiation than others, it may be concluded that the diamond comprises a synthetic diamond layer.

Again, it is strongly preferred that the observed radiation should include radiation substantially of wavelength 7 μm to 10 μm.

The means for observing radiation transmitted by parts of the stone may be the same as for the emission technique discussed above.

The diamond may be irradiated with infra red radiation by diffusely irradiating one side of the diamond and viewing it from the other side, by placing the diamond in an integrating sphere irradiated with infra red radiation or by irradiation with a fiber-optic probe.

The radiation used to irradiate the diamond preferably falls only in the band of interest. However, it would be possible to obtain results even if radiation falling outside the band of interest were also included.

Figure 2:
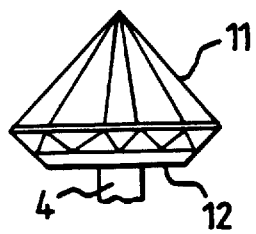
Figure 3:
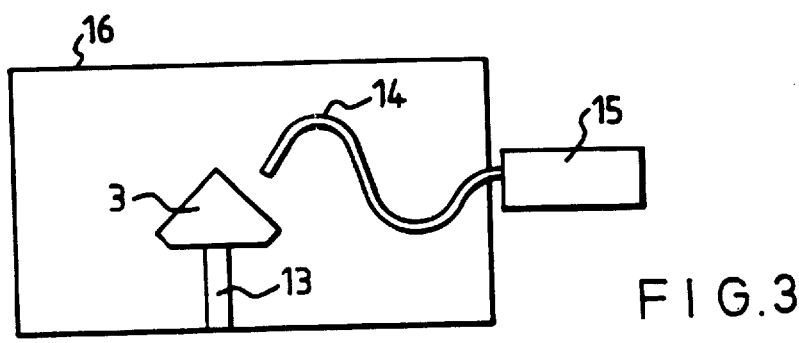

The invention will be further described by way of example only with reference to the accompanying drawings, in which:

FIG. 1 is a schematic illustration of a first embodiment of apparatus according to the invention;

FIG. 2 schematically shows an image of a CVD/natural diamond doublet produced by the first embodiment of the invention; and FIG. 3 is a schematic illustration of apparatus according to a second aspect of the invention.

The apparatus shown in FIG. 1 comprises apparatus for observing the infra red radiation emanating from a diamond, comprising imaging means 2 in the form of a thermal camera set up to image radiation of wavelengths falling in the range 8–12 μm. A diamond 3 can be placed in the apparatus, mounted on conventional diamond mounting means such as a dop 4 which allows the diamond to be manipulated and moved with respect to the thermal imaging camera 2 to allow different views of the diamond 3 to be taken.

The diamond 3 is viewed against a background 5. Means 6 and 7 may be provided to create a temperature difference between the diamond and the background to allow the diamond to be more clearly imaged. The means 6 comprise radiative heating means, for heating the diamond by infra red radiation. The means 6 emits radiation in a very broad band of wavelengths.

The background 5 is cooled by a cooled liquid pumped through the background by apparatus 7.

In order to provide a reference image of the diamond 3 to allow parts of the diamond 3 which are of interest to be more precisely located and interpreted, a lamp 8 is provided to illuminate the diamond 3 with visible radiation. The camera 2 may be such that it can image visible radiation, or an extra camera may be required.

The apparatus is contained in a light tight box 9 to prevent stray infra red radiation entering the imaging system 2.

The imaging system 2 produces an output on monitor 10 which can be studied by the operator.

FIG. 2 shows a typical image produced on the monitor 10. A CVD/natural diamond doublet mounted on a dop 4 is shown. Natural parts 11 of the stone appear relatively bright, CVD diamond material parts 12 appearing comparatively dark. The image will show a complex pattern of facets. A reference image may be produced using visible light from lamp 8, to distinguish such facets from features of different emissivity.

FIG. 3 shows an alternative apparatus according to the invention. The apparatus comprises diamond mounting means 13 such as a dop for mounting a diamond 3. A fiber-optic probe 14 is provided which may be contacted with the surface of the diamond 3 at a number of positions.

The fiber-optic probe 14 passes infra red radiation to a detector 15 which produces a reading or signal dependent upon the intensity of radiation emitted by the part of the stone in contact with the end of the fiber-optic probe 14. The fiber-optic probe 14 and diamond may be contained in a light tight box 16 to prevent stray infra-red radiation entering the detector 15.

The present invention has been described above purely by way of example, and modifications can be made within the invention. The invention also consists in any individual features described or implicit herein, or shown or implicit in the drawings or any combination of such features or any generalization of any such features or combinations.

We claim:

1. A method of testing whether a diamond has had a layer of synthetic diamond deposited thereon, comprising comparing observations of infra red radiation emanating from each of a plurality of zones of the diamond, to detect differences between the compositions of different zones of the diamond, the infra red radiation including radiation of wavelength substantially 7 μm to 25 μm.

2. The method of claim 1, wherein the infra red radiation emitted by said zones is observed.

3. The method of claim 2, wherein the infra red radiation emitted by said zones is observed by forming an image of the diamond.

4. The method of claim 3, wherein the image of the diamond is formed against a background which is at a different temperature to the diamond.

5. The method of claim 4, wherein the diamond is at a higher temperature than the background.

6. The method of claim 4 or 5, wherein the diamond is heated.

7. The method of claim 4 or 5, wherein the background is cooled.

8. The method of any of claims 2 to 5, wherein an image of the diamond is formed as viewed in a first direction relative to the diamond, at least one further image of the diamond being formed as viewed in a different direction relative to the diamond.

9. The method of any of claims 1 to 5, further comprising irradiating a plurality of different zones of the diamond with reference radiation which is substantially transmitted by all types of diamond or substantially absorbed by all types of diamond, and comparing observations of the reference radiation transmitted or reflected by the diamond with observations of the first mentioned radiation emanating from the diamond.

10. The method of claim 9, wherein an image of the reference radiation transmitted or reflected by the diamond is formed.

11. The method of claim 9, wherein the reference radiation comprises visible radiation.

12. The method of any of claim 1 to 5, further comprising the step of observing infra red radiation including radiation of wavelength substantially 7 μm to 25 μm emanating from zones of a diamond of known type and comparing observations of the known diamond and the diamond under test, to determine whether the diamond under test is of the same type as the known diamond.

13. The method of any of claims 1 to 5, further comprising the step of identifying the diamond as a CVD/natural diamond doublet, if the intensity of radiation emanating from some zones of the diamond is different to the radiation emanating from other zones.

14. The method of any of claims 1 to 5, wherein the radiation observed includes radiation of wavelength falling in the range substantially 7 μm to 10 μm.

15. The method of claim 1, wherein the radiation emanating from said zones is observed using radiation collecting means and a radiation detector.

16. The method of claim 15, wherein the diamond is placed in an integrating enclosure, the luminous flux intensity of the first mentioned radiation in the enclosure being detected by the detector.

17. The method of claim 15, wherein infra red radiation emitted by said zones is collected by a light guide and delivered thereby to the detector.

18. The method of claim 1, comprising irradiating the diamond with infra red radiation including radiation of wavelength substantially 7 μm to 25 μm, and observing radiation substantially of wavelength substantially 7 μm to 25 μm transmitted by different zones of the diamond.

19. The method of claim 18, wherein the radiation transmitted by said zones is observed by forming an image of the diamond.

20. Apparatus for testing whether a diamond has had a layer of synthetic diamond deposited thereon, comprising means for observing infra red radiation emanating from a zone of the diamond which is substantially smaller than the total surface area of the diamond, the infra red radiation including radiation of wavelength substantially 7 μm to 25 μm and means for forming an image of an area of the diamond including said zone.

21. The apparatus of claim 20, wherein the infra red radiation observed includes radiation of wavelength substantially 7 μm to 10 μm.

22. The apparatus of claim 20 to 21, further comprising mounting means for alterably mounting the position of the diamond with respect to the observing means.

23. The apparatus of claim 20, further comprising means for defining a background against which the diamond is imaged.

24. The apparatus of claim 23, further comprising means for creating a temperature difference between the diamond and the background.

25. The apparatus of claim 24, wherein the temperature difference creating means is for heating the diamond.

26. The apparatus of any one of claims 23 to 25, wherein the infra red radiation observed includes radiation of wavelength substantially 7 μm to 10 μm.

27. The apparatus of claim 24, wherein the temperature difference creating means is for cooling the background.

28. The apparatus of claim 20, wherein the means for observing the emitted infra red radiation comprises a radiation collector and a detector.

29. The apparatus of claim 28, wherein the radiation collector comprises a light guide for collecting infra red radiation emitted by said zone of the diamond and for delivering radiation thus collected to the detector.

30. The apparatus of any of claims 20, 21, 28, or 29, further comprising means for irradiating the diamond with reference radiation which is substantially transmitted by all types of diamond or substantially absorbed by all types of diamond, and means for observing reference radiation transmitted or reflected by the diamond.

31. The apparatus of claim 30, wherein an image of the transmitted or reflected reference radiation is formed.

32. The apparatus of claim 30, wherein the reference radiation comprises visible radiation.

33. The apparatus of claim 20, further comprising means for irradiating the diamond with infra red radiation including radiation of wavelength substantially 7 μm to 25 μm, the observing means being for observing radiation substantially of wavelength substantially 7 μm to 25 μm transmitted by said zone of the diamond.

34. The apparatus of claim 33, wherein the irradiating means is for irradiating the diamond with infra red radiation including radiation of wavelength substantially 7 μm to 10 μm and the observing means is for observing radiation of wavelength substantially 7 μm to 10 μm.

35. The apparatus of any of claims 20, 21, 28, 29, 33, or 34, wherein the means for observing infra red radiation is configured to examine a zone of the diamond which zone is substantially 0.5 mm across.

36. Apparatus for testing whether a diamond has had a layer of synthetic diamond deposited thereon, comprising means for observing infra red radiation emanating from a zone of the diamond which is substantially smaller than the total surface area of the diamond, the infra red radiation including radiation of wavelength substantially 7 μm to 25 μm, and mounting means for alterably mounting the position of the diamond with respect to the observing means.

37. Apparatus for testing whether a diamond has had a layer of synthetic diamond deposited thereon, comprising a radiation collector for collecting infra red radiation emanating from a zone of the diamond which is substantially smaller than the total surface area of the diamond, and a radiation detector for detecting the collected radiation of wavelength substantially 7 μm to 25 μm.

38. The apparatus of claim 37, wherein the radiation collector comprises a light guide for collecting infra red radiation emitted by said zone of the diamond and for delivering radiation thus collected to the detector.

39. Apparatus for testing whether a diamond has had a layer of synthetic diamond deposited thereon, comprising means for observing infra red radiation emanating from a zone of the diamond which is substantially smaller than the total surface area of the diamond, the infra red radiation including radiation of wavelength substantially 7 μm to 25

μm, means for irradiating the diamond with reference radiation which is substantially transmitted by all types of diamond or substantially absorbed by all types of diamond, and means for observing reference radiation transmitted or reflected by the diamond.

40. The apparatus of claim 39 including means for forming an image of the transmitted or reflected reference radiation.

41. The apparatus of claim 40, wherein the reference radiation comprises visible radiation.

42. The apparatus of claim 39 wherein the reference radiation comprises visible radiation.

43. Apparatus for testing whether a diamond has had a layer of synthetic diamond deposited thereon, comprising means for observing infra red radiation emanating from a zone of the diamond which is substantially smaller than the total surface area of the diamond, the infra red radiation including radiation of wavelength substantially 7 μm to 25 μm, and means for irradiating the diamond with infra red radiation including radiation of wavelength substantially 7 μm to 25 μm, the observing means being for observing radiation substantially of wavelength substantially 7 μm to 25 μm transmitted by said zone of the diamond.

44. The apparatus of claim 43 wherein the irradiating means is for irradiating the diamond with infra red radiation including radiation of wavelength substantially 7 μm to 10 μm and the observing means is for observing radiation of wavelength substantially 7 μm to 10 μm.

45. The apparatus of any one of claims 37 to 44, wherein the infra red radiation observed includes radiation of wavelength substantially 7 μm to 10 μm.

46. Apparatus for testing whether a diamond has had a layer of synthetic diamond deposited thereon, comprising support means for supporting a diamond, and means for observing infra red radiation emanating from a zone of a diamond supported by the support means which zone is substantially smaller than the total surface area of the diamond, the infra red radiation including radiation of wavelength substantially 7 μm to 25 μm, and wherein the infra red radiation observed includes radiation of wavelength substantially 7 μm to 10 μm.

47. The apparatus of claim 46 and further including a substantially light-light enclosure surrounding the support means.

* * * * *